(12) United States Patent
Lentz

(10) Patent No.: US 6,893,433 B2
(45) Date of Patent: May 17, 2005

(54) SYSTEM AND METHOD FOR PERFORMING A SINGLE STEP CRYOABLATION

(75) Inventor: David J. Lentz, La Jolla, CA (US)

(73) Assignee: CryoCor, Inc., San Diego, CA (US)

( * ) Notice: Subject to any disclaimer, the term of this patent is extended or adjusted under 35 U.S.C. 154(b) by 305 days.

(21) Appl. No.: 10/318,284

(22) Filed: Dec. 11, 2002

(65) Prior Publication Data

US 2004/0116917 A1 Jun. 17, 2004

(51) Int. Cl.$^7$ .............................................. A61B 18/02
(52) U.S. Cl. ............................ 606/23; 606/20; 600/113
(58) Field of Search ............... 606/20–26; 600/113–115

(56) References Cited

U.S. PATENT DOCUMENTS

| | | | |
|---|---|---|---|
| 4,838,268 A | | 6/1989 | Keith |
| 5,147,355 A | | 9/1992 | Friedman |
| 5,209,727 A | | 5/1993 | Radisch |
| 5,490,859 A | | 2/1996 | Mische |
| 5,516,336 A | | 5/1996 | McInnes |
| 5,865,802 A | * | 2/1999 | Yoon et al. ................. 604/104 |
| 6,012,457 A | | 1/2000 | Lesh |
| 6,024,740 A | | 2/2000 | Lesh |
| 6,149,574 A | | 11/2000 | Trauthen |
| 6,161,543 A | * | 12/2000 | Cox et al. .................... 128/898 |
| 6,237,355 B1 | | 5/2001 | Li |
| 6,245,064 B1 | | 6/2001 | Lesh |
| 6,562,030 B1 | | 5/2003 | Abboud et al. |
| 6,569,158 B1 | | 5/2003 | Abboud et al. |
| 6,575,933 B1 | | 6/2003 | Wittenberger et al. |
| 6,575,966 B2 | | 6/2003 | Lane et al. |
| 6,579,287 B2 | | 6/2003 | Wittenberger et al. |
| 6,585,717 B1 | | 7/2003 | Wittenberger et al. |
| 6,589,234 B2 | | 7/2003 | Lalonde et al. |
| 6,592,577 B2 | | 7/2003 | Abboud et al. |
| 6,595,988 B2 | | 7/2003 | Wittenberger et al. |
| 6,602,247 B2 | | 8/2003 | Lalonde |
| 6,629,972 B2 | | 10/2003 | Lehmann et al. |
| 6,635,053 B1 | | 10/2003 | Lalonde et al. |

* cited by examiner

Primary Examiner—Roy D. Gibson
Assistant Examiner—Aaron Roane
(74) Attorney, Agent, or Firm—Nydegger & Associates

(57) ABSTRACT

A system for cryoablating target tissue at a treatment site includes a cryo-element mounted at the distal end of a cryo-catheter. A balloon catheter is provided having a U-shaped balloon attached thereon. The cryo-element is threaded onto a pre-positioned guidewire and advanced within the patient's vasculature until the cryo-element is positioned at the treatment site. Next, the balloon is threaded onto the guidewire and advanced within the patient's vasculature using the balloon catheter. At the treatment site, the U-shaped balloon is interposed between the cryo-element and the target tissue. Saline solution is pumped into the balloon causing the U-shaped balloon to expand and contact both the cryo-element and the surrounding target tissue. Next, a refrigerant is expanded to cool the cryo-element, which in turn, freezes the saline solution. The resulting "ice ball" extracts heat from surrounding tissue resulting in the cryoablation of a substantially circumferential portion of tissue.

12 Claims, 3 Drawing Sheets

SYSTEM AND METHOD FOR PERFORMING A SINGLE STEP CRYOABLATION

FIELD OF THE INVENTION

The present invention pertains generally to systems and methods for cryoablating internal tissue. More particularly, the present invention pertains to systems and methods for cryoablating conduction blocks to treat patients experiencing heart arrhythmias such as atrial fibrillation. The present invention is particularly, but not exclusively, useful for creating substantially circumferential ablations surrounding the ostium of a pulmonary vein in a single step.

BACKGROUND OF THE INVENTION

Atrial fibrillation is an irregular heart rhythm that adversely affects approximately 2.5 million people in the United States. Anatomically, two pairs of pulmonary veins are connected to the left atrium of the heart with each pair delivering blood to the heart from one of the patient's lungs. It is believed that at least one-third of all atrial fibrillation originate near the ostium of the pulmonary veins.

It is further believed that the optimal technique to treat atrial fibrillation is to create circumferential lesions around the ostia where a pulmonary vein connects with the left atrium. More specifically, the goal is to ablate tissue to form a conduction block, to thereby prohibit the transmission of irregular electrical signals that can cause an arrhythmia. To be effective, the conduction block must completely block irregular signals and this often requires the ablation of a relatively deep, uniform lesion.

Heretofore, due to the relatively large diameters of these ostia, cryoablation procedures have required multiple, successive contacts between the cryo-element and the tissue around the periphery of an ostium. More specifically, these procedures have required the cryo-element to be successively moved around the ostia to create a patchwork array of ablations. This often results in a non-uniform circumferential ablation that fails to form an adequate conduction block. Furthermore, when successive contacts are prescribed, special catheter structures are generally required to give a catheter the agility required to carefully move from location to location within the pulmonary vein. These structures increase the size of the distal end of the catheter, making the catheter harder to steer and navigate through the vasculature of the patient to the treatment site. Is short, procedures requiring multiple contacts tend to be complicated, time consuming, difficult to perform, and generally unreliable.

Another factor that must be considered when ablating internal tissue is the stability of the ablation element (e.g. cryo-element) relative to the target tissue. During ablation, movements of the patient such as heartbeats and breathing can cause the ablation element to move or bounce. Failure to prevent these movements of the ablation element relative to the target tissue can disrupt the flow of energy between the ablation element and the tissue resulting in a non-uniform ablation. As indicated above, non-uniform ablations often result in an ineffective conduction block.

In light of the above, it is an object of the present invention to provide systems and methods suitable for the purposes of cryoablating substantially circumferential ablations of internal tissue in a single step. It is another object of the present invention to provide systems and methods for forming conductive blocks to treat heart arrhythmias such as atrial fibrillation. It is yet another object of the present invention to provide systems and methods for cryoablating internal target tissue that can be performed quickly and are relatively reliable.

SUMMARY OF THE INVENTION

The present invention is directed to a system and method for cryoablating internal target tissue at a treatment site. In one application of the system and method, a substantially circumferentially shaped portion of tissue surrounding the ostium of a pulmonary vein is ablated. The resulting lesion functions as a conduction block to treat heart arrhythmias such as atrial fibrillation.

For the present invention, the system includes a cryo-element mounted at the distal end of a cryo-catheter. The cryo-catheter can be tubular-shaped having a lumen that extends between the proximal and distal ends of the cryo-catheter. In one implementation, the cryo-element is formed with an expansion chamber that is placed in fluid communication with the lumen of the cryo-catheter when the cryo-element is mounted on the cryo-catheter.

The cryo-catheter can further include a supply tube that is positioned inside the lumen of the cryo-catheter. In one implementation, the supply tube is positioned inside the lumen of the cryo-catheter to establish a return line between the inner surface of the cryo-catheter and the outer surface of the supply tube. Furthermore, the supply tube can extend from the proximal end of the cryo-catheter to the distal end of the cryo-catheter.

The system further includes a refrigerant supply unit that is positioned at an extracorporeal location to introduce a fluid refrigerant into the proximal end of the supply tube. The fluid refrigerant then traverses through the lumen of the supply tube and exits the supply tube into the expansion chamber of the cryo-element. In one implementation, a flow restricting device such as a capillary tube is positioned upstream of the expansion chamber. In this implementation, fluid refrigerant in the supply tube passes through the restriction and then expands into the chamber to cool the cryo-element. In a particular embodiment of the present invention, a fluid refrigerant is used that transitions from a liquid state to a gaseous state as it expands into the cryo-element chamber. Heat absorbed by the refrigerant during this phase transition (i.e. latent heat) cools the cryo-element. After expansion, the gaseous fluid refrigerant passes through the return line and exits the patient at the proximal end of the cryo-catheter.

The system of the present invention further includes a balloon and a balloon catheter for interposing the balloon between the cryo-element and the target tissue. For the present invention, the balloon catheter is elongated and defines a longitudinal axis in the direction of elongation. In more detail, the balloon catheter is formed with a lumen that extends between the proximal and distal ends of the balloon catheter. The balloon is attached to the distal end of the balloon catheter and is placed in fluid communication with the lumen of the balloon catheter. With this combination of structure, a saline solution can be introduced into the balloon by pumping saline solution into the proximal end of balloon catheter at an extracorporeal location. Structurally, when inflated with a saline solution, the balloon has a substantially U-shaped cross-section in a plane substantially orthogonal to the longitudinal axis of the balloon catheter. This shape allows the balloon to surround and grip the cryo-element, and to conductively transfer heat from the target tissue through the inflated balloon to the cryo-element along substantially radial paths.

In operation, the tip of a guidewire is first inserted into the vasculature of the patient and advanced past the target tissue.

Next, an eyelet attached to the cryo-catheter is threaded onto the guidewire and the cryo-element is advanced through the vasculature of the patient using the cryo-catheter until the cryo-element is positioned at the treatment site. With the cryo-element in place, an eyelet attached to the balloon catheter is then threaded onto the guidewire allowing the balloon to be advanced within the patient's vasculature to the treatment site using the balloon catheter. At the treatment site, the U-shaped balloon can be interposed between the cryo-element and the target tissue. Alternatively, depending on the particular requirements for a procedure, the balloon can be positioned either distal or proximal to the cryo-element.

With the balloon interposed between the cryo-element and the target tissue, saline solution is pumped into the balloon causing the balloon to expand. Filling of the balloon with saline solution is continued until the expanded balloon contacts both the cryo-element and the surrounding target tissue. The shape of the balloon (i.e. the U-shape) allows the balloon to surround the cryo-element and provide a large contact area between the balloon and the cryo-element. The large contact area, in turn, provides for good heat transfer between the saline solution and the cryo-element. In addition, the expanded balloon functions to anchor the cryo-element in place at the site of the target tissue.

Once the balloon has been adequately filled with liquid, the refrigerant supply unit is activated to introduce a fluid refrigerant into the expansion chamber of the cryo-element and thereby cool the cryo-element. In one implementation, nitrous oxide is used as the refrigerant allowing the cryo-element to be cooled to a temperature of approximately –85 degrees Celsius. The cooling of the cryo-element, in turn, freezes and cools the liquid in the balloon to a temperature of approximately –85 degrees Celsius. The freezing creates an "ice ball" that extracts heat from surrounding tissue resulting in the cryoablation of a substantially circumferential portion of tissue.

The system can also include a mechanism for directing energy into the "ice ball" to quickly thaw the frozen "ice ball" and restore blood flow through the affected conduit (e.g. pulmonary vein). Once the "ice ball" is thawed, the saline solution can be removed from the balloon and the balloon withdrawn from the patient's body. In one embodiment of the present invention, the system includes a radiofrequency (rf) antenna positioned near the balloon to thaw the "ice ball" and facilitate removal of the balloon from the patient.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
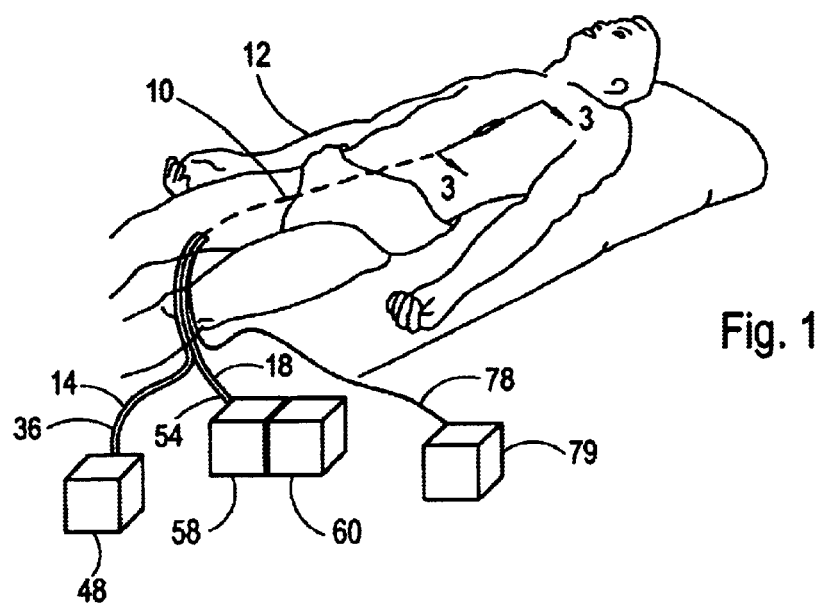
FIG. 1 is a perspective view of a system for ablating internal target tissue shown with the distal end of the system positioned at a treatment site in the patient and with peripheral components of the system shown schematically.

Referring initially to FIG. 1, a system 10 for cryoablating internal target tissue of a patient 12 is shown. As shown, the system 10 includes the cryo-catheter 14 for positioning a cryo-element 16 (see FIG. 2) and a balloon catheter 18 for positioning a balloon 20 at an internal treatment site of the patient 12. As further shown in FIG. 1, both the cryo-catheter 14 and balloon catheter 18 can be inserted into a peripheral artery of the patient 12 such as the femoral artery and advanced through the vasculature to a position in the upper body of the patient 12.

Figure 2:
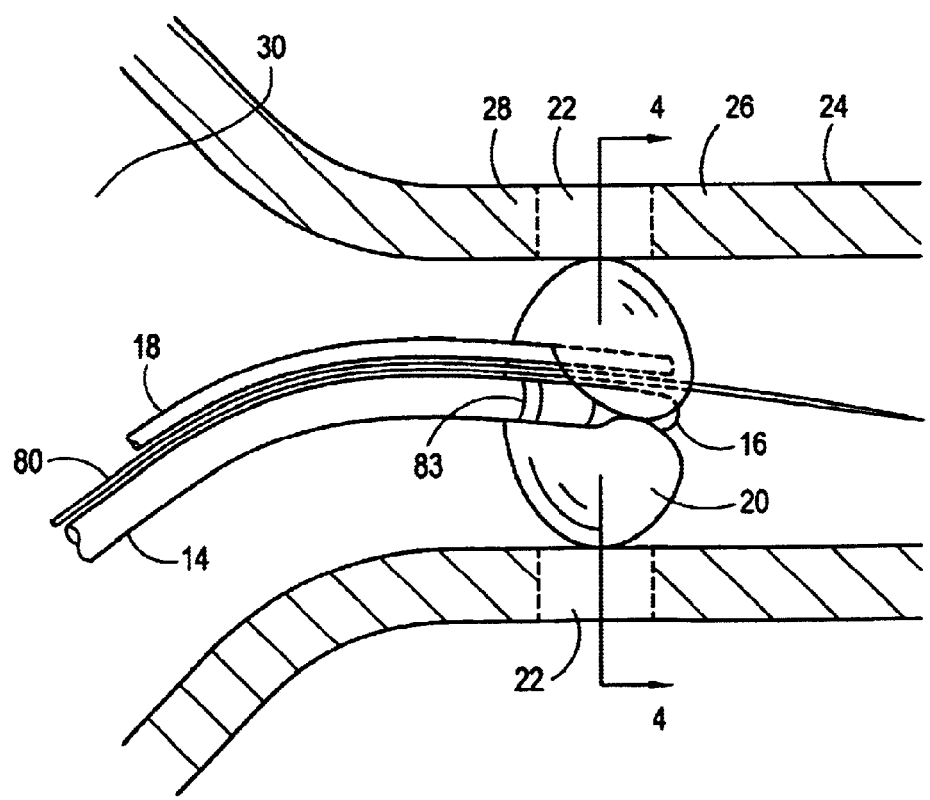
FIG. 2 is a perspective view of the distal end of a system for ablating internal target tissue shown positioned in a pulmonary vein.

Referring now to FIG. 2, an application of the system 10 is shown wherein a substantially circumferential target tissue 22 surrounding the ostium of a pulmonary vein 24 is ablated. The resulting lesion, which can extend through the wall of the pulmonary vein 24 as shown, can function as a conduction block to prevent the transmission of electrical signals. In greater detail, the lesion can prevent electrical signals traveling toward the target tissue 22 from exemplary area 26 of the pulmonary vein 24 from passing through the ablated target tissue 22 to exemplary area 28. By preventing the transmission of these electrical signals, the ablated target tissue 22 can be used to treat heart arrhythmias such as atrial fibrillation. FIG. 2 further shows that the distal end of the system 10 can be passed through the left atrium 30 to access the pulmonary vein 24 and ablate the target tissue 22.

Figure 3:
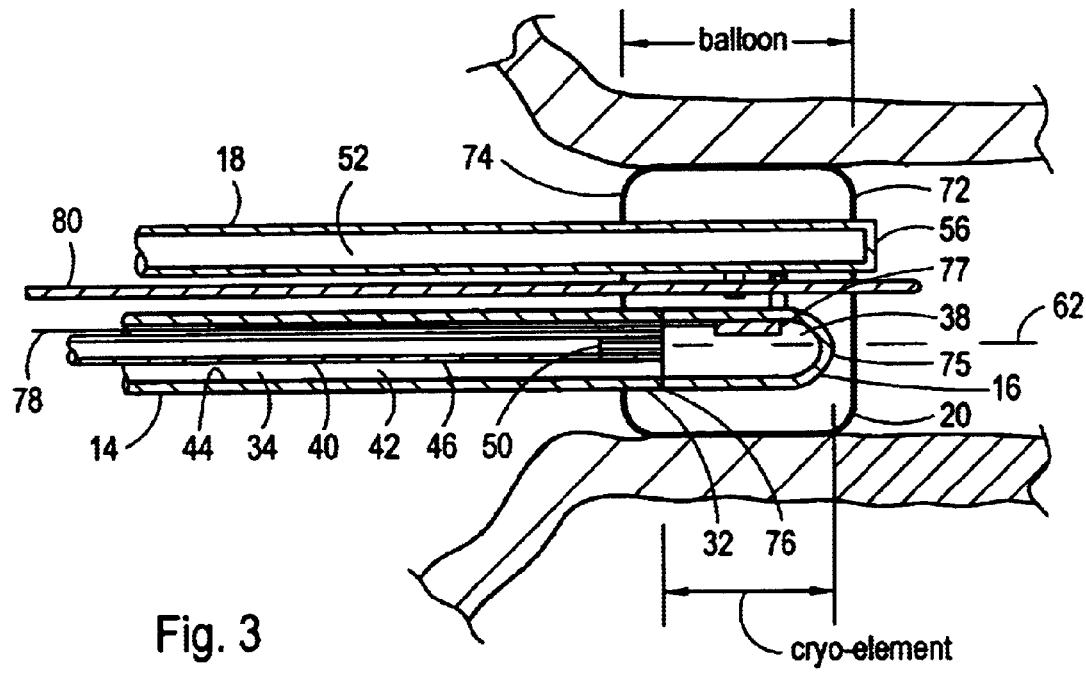
FIG. 3 is a sectional view of the distal end of the system shown in FIG. 2 as seen along line 3—3 in FIG. 1.

With reference now to FIG. 3, it can be seen that the cryo-element 16 is mounted on cryo-catheter 14 at the distal end 32 of the cryo-catheter 14. As further shown, the cryo-catheter 14 is tubular-shaped having a lumen 34 that extends from the proximal end 36 (see FIG. 1) to the distal end 32 of the cryo-catheter 14. Also shown in FIG. 3, the cryo-element 16 is formed with an expansion chamber 38 that is placed in fluid communication with the lumen 34 of the cryo-catheter 14.

Continuing with FIG. 3, the cryo-catheter 14 can further include a supply tube 40 that is positioned inside the lumen 34 of the cryo-catheter 14. It can be further seen that the supply tube 40 is positioned inside the lumen 34 of the cryo-catheter 14 to establish a return line 42 between the inner surface 44 of the cryo-catheter 14 and the outer surface 46 of the supply tube 40. For the system 10, the supply tube 40 can extend from the proximal end 36 of the cryo-catheter 14 to the distal end 32 of the cryo-catheter 14.

With cross reference now to FIGS. 1 and 3, it can be seen that system 10 further includes a refrigerant supply unit 48 that is positioned at an extracorporeal location to introduce a fluid refrigerant into the supply tube 40 at the proximal end 36 of the cryo-catheter 14. The fluid refrigerant then traverses through the supply tube 40 and enters the expansion chamber 38 of the cryo-element 16. As shown in FIG. 3, a flow restricting device 50, such as a capillary tube, can be inserted in the supply tube 40 at the distal end 32 of the cryo-catheter 14. With this cooperation of structure, fluid refrigerant in the supply tube 40, passes through the flow restricting device 50 and then expands into the chamber 38 to cool the cryo-element 16.

In one embodiment of the present invention, a fluid refrigerant is used that transitions from a liquid state to a gaseous state as it expands into the expansion chamber 38 of the cryo-element 16. A suitable refrigerant supply unit 48 for delivering a refrigerant in a liquid state to the distal end 32 of the cryo-catheter 14 for transition to a gaseous state in the expansion chamber 38 is disclosed in co-pending U.S. patent application Ser. No. 10/243,997, entitled "A Refrigeration Source for a Cryoablation Catheter" and filed on Sep. 12, 2002, which is assigned to the same assignee as the present invention. Co-pending U.S. patent application Ser. No. 10/243,997 is incorporated by reference herein. Heat absorbed by the refrigerant during this phase transition (i.e. latent heat) cools the cryo-element 16. After expansion, the gaseous fluid refrigerant passes through the return line 42 and exits the patient 12 at the proximal end 36 of the cryo-catheter 14. In one implementation, nitrous oxide is used as the refrigerant with suction applied to the return line 42 allowing the cryo-element 16 to be cooled to a temperature of approximately −85 degrees Celsius.

Figure 4:
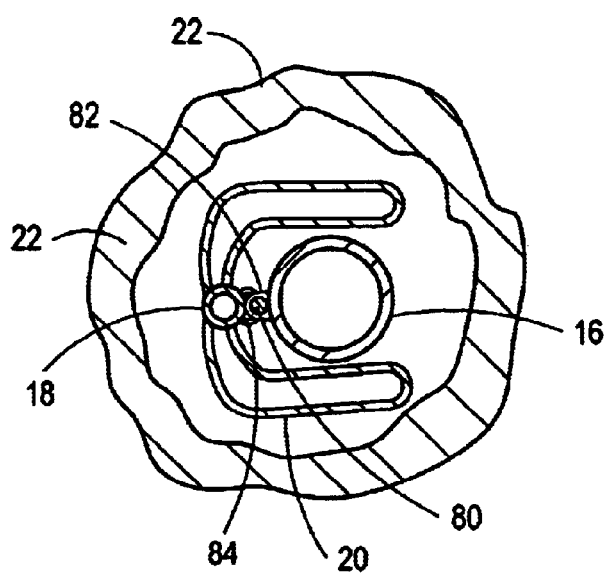
FIG. 4 is a sectional view of the system shown in FIG. 2 as seen along line 4—4 in FIG. 2 showing the balloon in the collapsed configuration.
Figure 5:
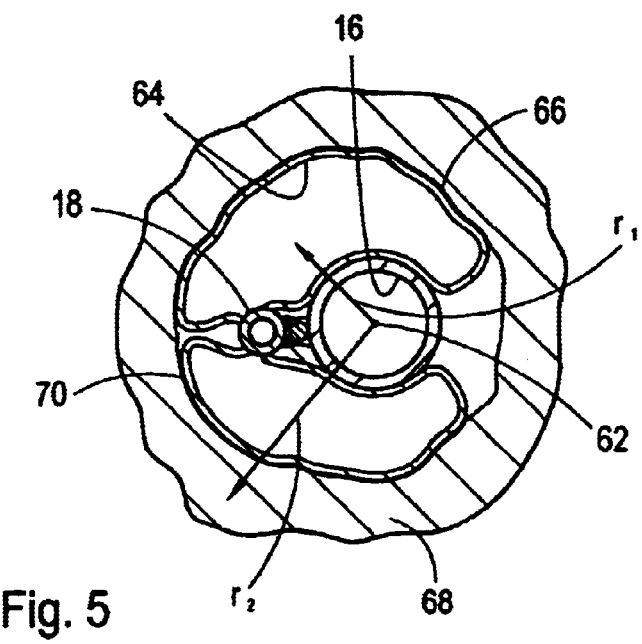
FIG. 5 is a sectional view as in FIG. 4 showing the balloon in the expanded configuration.

With cross-reference now to FIGS. 3, 4 and 5, it can be seen that the system 10 includes a balloon 20 that can be configured in a collapsed configuration (see FIG. 4) to allow the collapsed balloon 20 to be advanced through the vasculature of the patient 12. While the balloon 20 is in the collapsed configuration, the balloon catheter 18 can be used to interpose the collapsed balloon 20 between the cryo-element 16 and the target tissue 22. As best seen in FIG. 3, the balloon catheter 18 is formed with a lumen 52 that extends between the proximal end 54 (see FIG. 1) of the balloon catheter 18 and distal end 56 of the balloon catheter 18. As further shown, the balloon 20 is attached to the distal end 56 of the balloon catheter 18 and placed in fluid communication with the lumen 52 of the balloon catheter 18. With this combination of structure, a pump 58 can be used to introduce saline solution from a reservoir 60 into the proximal end 54 of balloon catheter 18 for introduction into the balloon 20 to reconfigure the balloon 20 into an expanded configuration (see FIG. 4).

With cross-reference now to FIGS. 3 and 5, it can be seen that the balloon 20 defines a balloon axis 62 and that the balloon 20 has a substantially U-shaped cross-section in a plane substantially orthogonal to the balloon axis 62. This shape allows the balloon 20, when expanded (see FIG. 5) to surround the cryo-element 16 and transfer heat from the target tissue 22 to the cryo-element 16 along substantially radial paths. As shown in FIG. 5, the balloon 20 has an interior surface 64 for contacting the saline solution and an exterior surface 66. Also shown, the exterior surface 66 is formed with an inner surface portion 68 for forming a crook to surround and contact the cryo-element 16 and a projected outer surface portion 70 for contacting a substantially circumferential shaped target tissue 22.

It can be further seen that the inner surface portion 68 has a substantially constant radius $r_1$ about the balloon axis 62 and the outer surface portion 70 has a substantially constant radius $r_2$ about the balloon axis 62, with $r_1 < r_2$. As best seen in FIG. 3, the balloon 20 extends from a distal end 72 to a proximal end 74 and defines a balloon length, $l_{balloon}$ therebetween. Further, the cryo-element 16 extends from a distal end 75 to a proximal end 76 and defines a cryo-element length, $l_{cryo-element}$ therebetween. FIG. 3 further shows that the balloon 20 can have a balloon length that is longer than the cryo-element length ($l_{balloon} > l_{cryo-element}$) to allow the expanded balloon 20 to surround the cryo-element 16 at the distal end 75 and proximal end 76 of the cryo-element 16.

With cross-reference to FIGS. 1 and 3, it can be seen that the system 10 also includes a radiofrequency (RF) antenna 77, which can be used to generate heat to quickly thaw frozen saline solution and restore blood flow through the affected conduit (e.g. pulmonary vein 24). As shown, the RF antenna 77 is electrically connected via wire 78 to signal generator 79 that is positioned at an extracorporeal location. Although the RF antenna 77 is shown positioned in the expansion chamber 38, it is to be appreciated that the RF antenna 77 could also be mounted on either the cryo-catheter 14 or the balloon catheter 18. It is to be further appreciated by the skilled artisan that an RF electrode (not shown) can be used in place of the RF antenna 77 to generate a current for receipt by a return electrode (also not shown) to thaw the frozen saline solution.

Figure 6:
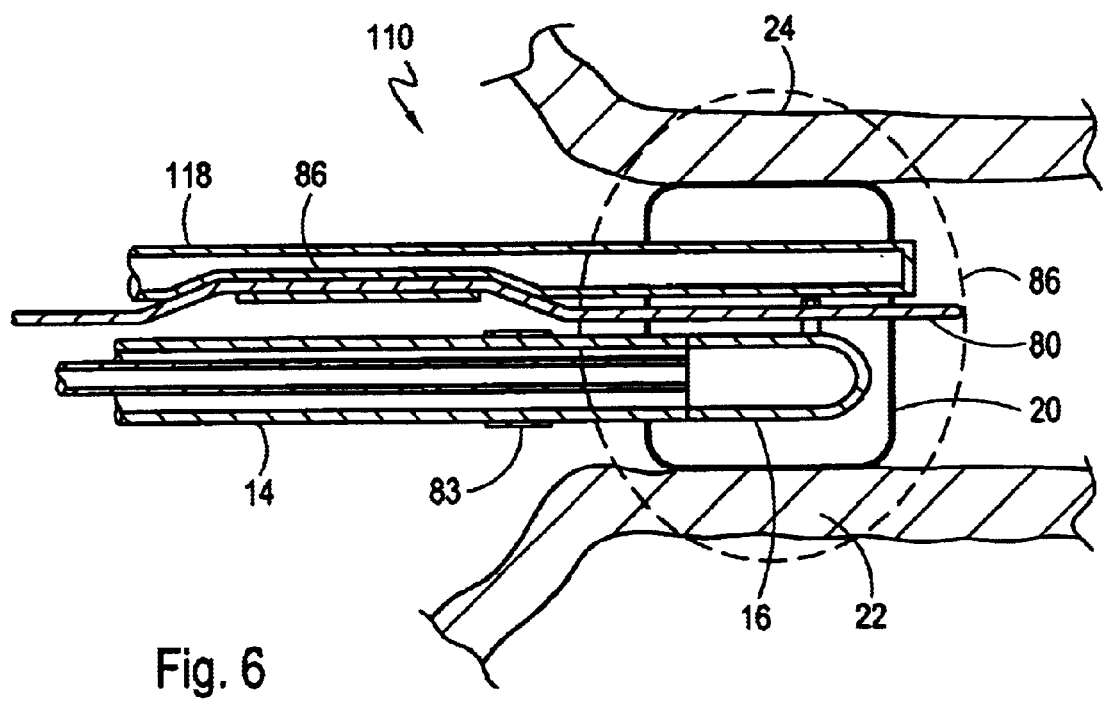
FIG. 6 is a sectional view as in FIG. 3 showing an alternate embodiment of a system for ablating internal target tissue wherein the balloon catheter is formed with a lumen for tracking the guidewire.

The operation of the system 10 can best be appreciated with initial reference to FIGS. 1 and 2. First, the distal tip of a guidewire 80 is inserted into the vasculature of the patient 12, for example using a peripheral artery, and advanced past the target tissue 22. As discussed above, for ablation at the ostium of the pulmonary vein 24, the guidewire 80 can be passed through the left atrium 30 of the patient's heart and into the pulmonary vein 24. With the guidewire 80 in place, and eyelet 82 mounted on the cryo-element 16 (see FIG. 4) is threaded onto the guidewire 80 and the cryo-element 16 is advanced within the vasculature of the patient 12 using the cryo-catheter 14 until the cryo-element 16 is positioned at the treatment site. In one implementation a radiopaque marker 83 (see FIG. 2) attached to the cryo-catheter 14 can be used to position the cryo-element 16 at the treatment site. Once the cryo-element 16 is in place, the balloon 20 is collapsed and an eyelet 84 that is attached to the balloon catheter 18 is then threaded onto the guidewire 80. The collapsed balloon 20 is then advanced within the patient's vasculature using the balloon catheter 18. At the treatment site, the U-shaped balloon 20 is interposed between the cryo-element 16 and the target tissue 22, as shown in FIG. 4. As shown in FIG. 6, in an alternate embodiment of the system (designated 110), the balloon catheter (designated 118) can be formed with a guidewire lumen 86 for tracking the guidewire 80.

With cross-reference now to FIGS. 4 and 5, it can be seen that with the collapsed balloon 20 interposed between the cryo-element 16 and the target tissue 22, pump 58 (shown in FIG. 1) can be activated to introduce saline solution into the balloon 20 to cause the balloon 20 to expand (expanded balloon shown in FIG. 5) and contact both the cryo-element 16 and the surrounding target tissue 22. It will be appreciated by the skilled artisan that instead of being a "collapsed" balloon 20, the balloon 20 can be a so-called "free blown" balloon 20 made of an elastomeric material that stretches during inflation. In either case, as shown in FIG. 5, the shape of the balloon 20 (i.e. the U-shape) allows the balloon 20 to surround the cryo-element 16 and provide a large contact area between the balloon 20 and the cryo-element 16. The large contact area, in turn, provides for good heat transfer between the saline solution in the balloon 20 and the cryo-element 16. Additionally, the expanded balloon 20 functions to anchor the cryo-element 16 in place at the site of the target tissue 22.

Cross-referencing now to FIGS. 1 and 3, after the balloon 20 has been adequately filled with saline solution, the refrigerant supply unit 48 is activated to introduce a fluid refrigerant into the expansion chamber 38 of the cryo-element 16 and thereby cool the cryo-element 16. As indicated above, in one implementation of the system 10, nitrous oxide is used as the refrigerant allowing the cryo-element 16 to be cooled to a temperature of approximately −85 degrees Celsius. The cooling of the cryo-element 16, in turn, freezes and cools the saline solution in the balloon 20 to a temperature of approximately −85 degrees Celsius. This cooling can result in the formation of an "ice ball" (indicated by dash line 88 in FIG. 6) that includes the frozen saline solution and can include frozen blood in the pulmonary vein 24. The ice ball 88 extracts heat from target tissue 22 resulting in the cryoablation of a substantially circumferential portion of target tissue 22.

After the target tissue 22 has been successfully cryoablated, the signal generator 79 can be activated to generate heat via RF antenna 77 to quickly thaw the frozen ice ball 88 and restore blood flow through the affected conduit (e.g. pulmonary vein 24). Once the ice ball 88 is thawed, the saline solution can be removed from the balloon 20 and the balloon 20 withdrawn from the patient's body or moved to another treatment site such as another pulmonary vein for further cryo-ablation.

While the particular System And Method For Performing A Single Step Cryoablation as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A system for cryoablating target tissue of a patient at a treatment site, said system comprising:

a first catheter;

a cryo-element attached to said first catheter, said first catheter for positioning said cryo-element at the treatment site;

a second catheter;

a balloon attached to said second catheter for interposing said balloon between said cryo-element and with the target tissue;

means for introducing a liquid into said balloon to expand said balloon, wherein said expanded balloon is substantially U-shaped to form a crook for fixedly holding said cryo-element therein and to urge an outer projected surface portion of said expanded balloon into contact with the target tissue; and means for cooling said cryo-element to freeze said liquid and cryoablate the target tissue.

2. A system as recited in claim 1 wherein said balloon defines a balloon axis with at least one balloon section normal to said balloon axis being substantially U-shaped, said balloon formed with an inner surface portion having a substantially constant radius $r_1$ about said balloon axis for contacting said cryo-element and an outer surface portion having a substantially constant radius $r_2$ about said balloon axis for contacting target tissue, with $r_1<r_2$.

3. A system as recited in claim 1 wherein said balloon has a distal end and a proximal end and defines a balloon length, $l_{balloon}$ therebetween, said cryo-element has a distal end and a proximal end and defines a cryo-element length, $l_{cryo-element}$ therebetween and wherein said balloon length, is longer than said cryo-element length ($l_{balloon}>l_{cryo-element}$) to allow said balloon to surround said cryo-element.

4. A system as recited in claim 1 further comprising a radiopaque marker attached to said first catheter.

5. A system as recited in claim 1 wherein said cryo-element is formed with an expansion chamber to allow a fluid to expand therein and cool said cryo-element.

6. A system as recited in claim 1 wherein said liquid comprises a saline solution.

7. A system as recited in claim 1 further comprising a radiofrequency antenna attached to one of said first and second catheters to thaw said frozen liquid after cryoablation of the target tissue to allow for removal of said balloon from the patient.

8. A system for cryoablating target tissue of a patient at a treatment site, said system comprising:

a first catheter;

a cryo-element formed with a chamber attached to said first catheter, said first catheter for positioning said cryo-element at the treatment site;

a second catheter;

a balloon attached to said second catheter, said second catheter for interposing said balloon between said cryo-element and with the target tissue;

a liquid reservoir;

a pump in fluid communication with said reservoir and said balloon, said pump for transferring liquid from said reservoir to said balloon to expand said balloon, wherein said balloon is substantially U-shaped to form a crook for fixedly holding said cryo-element therein and to urge an outer projected surface portion of said expanded balloon into contact with the target tissue; and a refrigerant supply unit for delivering a refrigerant to said cryo-element for expansion of said refrigerant in said chamber to freeze said liquid and cryoablate the target tissue.

9. A system as recited in claim 8 wherein said balloon defines a balloon axis with at least one balloon section normal to said balloon axis being substantially U-shaped, said balloon formed with an inner surface portion having a substantially constant radius $r_1$ about said balloon axis for contacting said cryo-element and an outer surface portion having a substantially constant radius $r_2$ about said balloon axis for contacting target tissue, with $r_1<r_2$.

10. A system as recited in claim 8 wherein said balloon has a distal end and a proximal end and defines a balloon length, $l_{balloon}$ therebetween, said cryo-element has a distal end and a proximal end and defines a cryo-element length, $l_{cryo-element}$ therebetween and wherein said balloon length, is longer than said cryo-element length ($l_{balloon}>l_{cryo-element}$) to allow said balloon to surround said cryo-element.

11. A system as recited in claim 8 further comprising a radiopaque marker attached to said first catheter for locating the position of said first catheter in the patient.

12. A system as recited in claim 9 further comprising a radiofrequency antenna positioned on one of said first and second catheters to thaw said frozen liquid after cryoablation of the target tissue to allow for removal of said balloon from the patient.

* * * * *

UNITED STATES PATENT AND TRADEMARK OFFICE
CERTIFICATE OF CORRECTION

PATENT NO. : 6,893,433 B2
DATED : May 17, 2005
INVENTOR(S) : David J. Lentz

It is certified that error appears in the above-identified patent and that said Letters Patent is hereby corrected as shown below:

Column 8,
Line 11, delete "crycablating" insert -- cryoablating --
Line 56, delete "9" insert -- 8 --

Signed and Sealed this

Nineteenth Day of July, 2005

JON W. DUDAS
*Director of the United States Patent and Trademark Office*